United States Patent [19]
Koot

[11] Patent Number: 6,150,548
[45] Date of Patent: Nov. 21, 2000

[54] LINKERS

[75] Inventor: Wim-Jan Koot, Kersenlaan, Netherlands

[73] Assignee: Akzo Nobel, N.V.

[21] Appl. No.: 09/247,287

[22] Filed: Feb. 9, 1999

[30] Foreign Application Priority Data

Feb. 13, 1998 [EP] European Pat. Off. ............... 98200465

[51] Int. Cl.$^7$ ................................. C07F 7/02; C07F 7/04; C07F 7/08; G01N 33/53; C07K 5/00

[52] U.S. Cl. ........................... 556/413; 556/400; 556/418; 556/423; 556/428; 556/437; 556/448; 556/465; 556/466; 556/478; 530/333; 530/334; 435/7.1; 435/7.2; 436/501; 436/518; 525/342

[58] Field of Search ...................... 435/7.1, 7.2; 436/501, 436/518; 530/333, 334; 556/400, 413, 418, 465, 423, 466, 428, 478, 437, 448

[56] References Cited

FOREIGN PATENT DOCUMENTS

WO 9516712  6/1995  WIPO.

OTHER PUBLICATIONS

Blackburn et al. Functionalized Resins and Linkers for Solid–Phase Synthesis of Small Molecules. Drugs of the Future. vol. 22, No. 9, pp. 1007–1025, 1997.

*Primary Examiner*—Jyothsna Venkat
*Assistant Examiner*—Maurie E. Garcia
*Attorney, Agent, or Firm*—Mary E. Gormley

[57] ABSTRACT

The invention relates to a compound having the formula I

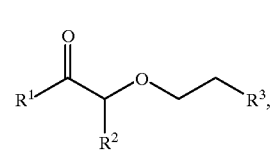

(I)

wherein $R^1$ is hydroxy, (1–6C)alkoxy or $NR^4R^5$, $R^4$ and $R^5$ being independently hydrogen, (1–6C)alkyl, (3–7C)cycloalkyl, (2–6C)alkenyl, (4–6C)aryl or (5–7C)aralkyl, the aryl groups of which may be optionally substituted with halogen, (1–6C)alkyl or (1–6C)alkoxy;

$R^2$ is a halo atom, (1–8C)acyloxy, —O—C(O)—O-(1–6C)alkyl, —O—C(O)—O-(5–7C)aralkyl, —$SR^6$, —$S(O)R^6$, —$SeR^6$ or —$Se(O)R^6$, $R^6$ being (1–6C)alkyl or (4–6C)aryl; and $R^3$ is —$Si(R^7)_3$, $R^7$ being independently (1–6C)alkyl or (4–6C)aryl. The compounds of the invention may be used as protective groups or as linkers in solid phase organic chemistry.

18 Claims, No Drawings

LINKERS

FIELD OF THE INVENTION

The invention relates to new compounds and methods for their use, which find application in solid phase chemical syntheses, e.g. in combinatorial organic chemistry. This includes the preparation of small molecules and libraries thereof as well as the preparation of polymer sequences of such small molecules.

The compounds of the present invention are those which are typically referred to as linking groups, linkers or spacers.

BACKGROUND OF THE INVENTION

In the past few years, combinatorial chemistry has been recognised as a very useful tool for the synthesis of large numbers of different compounds in a relatively short period of time. This gave an enormous impetus to the research relating to the development of reaction conditions suitable for combinatorial chemistry, and in particular, for solid phase organic chemistry (SPOC). For instance, there is a continuous search for new linkers.

Various linkers are known to be useful in SPOC. Often the choice of linker depends on the specific requirements of the particular type of organic reactions to be performed. Thus, there are acid-sensitive, base-sensitive, nucleophilic-sensitive, electrophilic sensitive, photosensitive, oxidation sensitive or reduction sensitive types of linkers. Also selectively cleavable linkers may be employed. Combinations of such linkers may be used to allow sequential cleaving from a solid support.

A highly important class of linkers are those cleavable under mild, neutral conditions, thus allowing the use and production of complex and sensitive molecules. The application of fluoride induced cleavage offers a mild, essentially neutral, alternative for photolytic, basic or acidic cleavage techniques. Linkers, suitable for this type of cleavage, are e.g. silicium-based linkers. A number of such linkers have already been described. However, many suffer from (technical) drawbacks, such as the fact that they have to be attached to the ligand molecule prior to their attachment to the support (*Tetrahedron Lett.* 1987, 28, 4105; *J.Org.Chem.* 1995, 60, 6006; *J.Org.Chem.* 1996, 61, 6498) and/or a lengthy synthesis (*Tetrahedron Lett.* 1998, 39, 897; *J.Org.Chem.* 1988, 53, 5240). Other reported silicium-based linkers (*Tetrahedron Lett.* 1997, 38, 8287) are significantly less stable towards acids than the linkers of the present invention.

SUMMARY OF THE INVENTION

The present invention relates to a new class of silicium-based linkers which can be prepared using relatively easy synthetic methods, which can be attached to the solid support before a ligand molecule is attached to the linker, and which are useful in a broad range of solid phase synthetic methods.

The compounds of the present invention, which may also be used as protective groups, have the formula I

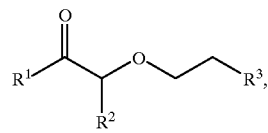

(I)

wherein $R^1$ is hydroxy, (1–6C)alkoxy or $NR^4R^5$, $R^4$ and $R^5$ being independently hydrogen, (1–6C)alkyl, (3–7C)cycloalkyl, (2–6C)alkenyl, (4–6C)aryl or (5–7C)aralkyl, the aryl groups of which may be optionally substituted with halogen, (1–6C)alkyl or (1–6C)alkoxy;

$R^2$ is a halo atom, (1–8C)acyloxy, —O—C(O)—O-(1–6C)alkyl, —O—C(O)—O-(5–7C)aralkyl, —$SR^6$, —$S(O)R^6$, —$SeR^6$ or —$Se(O)R^6$, $R^6$ being (1–6C)alkyl or (4–6C)aryl; and $R^3$ is —$Si(R^7)_3$, $R^7$ being independently (1–6C)alkyl or (4–6C)aryl.

DETAILED DESCRIPTION OF THE INVENTION

Preferred compounds of formula I are compounds wherein $R^3$ is $SiMe_3$, $SiEt_3$, $SiMe_2t$-Bu, $SiMe_2Ph$. More preferred are the compounds wherein $R^1$ is hydroxy or (1–6C)alkoxy. In particular preferred are those compounds wherein $R^2$ is a halo atom, —O—C(O)—O-(1–6C)alkyl or —$SeR^6$. The most preferred compounds of formula I are those wherein $R^1$ is methoxy; $R^2$ is chlorine, —O—C(O)—O-t-Bu or —Se-phenyl; and $R^3$ is —$SiMe_3$.

The compounds of formula I according to this invention may be prepared according to well known methods described and used in organic chemistry. In this respect, in particular reference is made to *Tetrahedron Lett.* 1980, 21, 3343; *Syn. Commun.* 1984, 14, 83 and *Tetrahedron Lett.* 1988, 29, 6365. A suitable process for the preparation of the compounds of formula I is characterized by a process comprising the following steps: a glyoxylic acid or a derivative thereof of formula Ia,

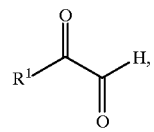

(Ia)

wherein $R^1$ has the previously defined meaning, is acetalized with $R^3(CH_2)_2OH$, wherein $R^3$ has the previously defined meaning, to form a compound of formula Ib

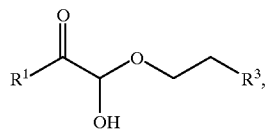

(Ib)

the hydroxy functionality of which is subsequently protected/activated (e.g. by reaction with an acylanhydride or a dialkyl pyrocarbonate, such as (t-Boc)$_2$O), thus forming the compounds of formula I wherein $R^2$ is (1–8C)acyloxy, —O—C(O)—O-(1–6C)alkyl, —O—C(O)—O-(5–7C)

aralkyl, optionally followed by nucleophilic substitution by a halogen of the thus activated hydroxy group (e.g. by using hydrogen chloride in diethyl ether), optionally followed by a nucleophilic substitution reaction (using a base and a suitable nucleophile in an appropriate solvent) by which the halogen is replaced by —SR$^6$ or —SeR$^6$, R$^6$ having the previously defined meaning, optionally followed by oxidation to obtain the compounds of formula I wherein R$_2$ is —S(O)R$^6$ or —Se(O)R$^6$.

As stated earlier, the compounds of the present invention are useful as linkers in solid phase organic chemistry and as protective groups. If used for the latter purpose, the compounds are reacted under suitable conditions with an appropriate substrate molecule which needs protection of a hydroxy functionality (e.g. as described in T. W. Greene et al., *Protective Groups in Organic Synthesis*, 2nd Ed., John Wiley & Sons, Inc., New York (1991)). Thereby the group R$^2$ is replaced by the substrate molecule, which at any later stage may be removed therefrom upon application of a mild chemical cleaving reagent (e.g. fluoride induced cleavage).

A major use of the compounds of the present invention relates to their use when attached to a solid phase support. Therefore, compositions of the formula II are a further aspect of the present invention:

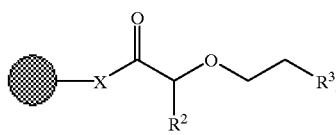

(II)

wherein the symbol

represents a solid phase support; X is a bond or a derivatizing group;

R$^2$ is a halo atom, (1–8C)acyloxy, —O—C(O)—O-(1–6C)alkyl, —O—C(O)—O-(5–7C)aralkyl, —SR$^6$, —S(O)R$^6$, —SeR$^6$ or —Se(O)R$^6$, R$^6$ being (1–6C) alkyl or (4–6C)aryl; and R$^3$ is —Si(R$^7$)$_3$, R$^7$ being independently (1–6C)alkyl or (4–6C)aryl.

Preferred compositions of formula II are those wherein R$^3$ is SiMe$_3$, SiEt$_3$, SiMe$_2$t-Bu, SiMe$_2$Ph. More preferred are the compositions wherein R$^2$ is a halo atom, —O—C(O)—O-(1–6C)alkyl or —SeR$^6$. The most preferred compositions of formula II are those wherein R$^2$ is chlorine, —O—C(O)—O-t-Bu or —Se-phenyl; and R$^3$ is —SiMe$_3$.

The compositions of formula II according to this invention may be prepared according to well known methods described and used in solid phase organic chemistry. In this respect, in particular reference is made to *Synthesis* 1984, 572 and *Tetrahedron Lett.* 1989, 30, 1927. A suitable process for the preparation of the compositions of formula II is characterized by a process comprising the following steps:

(A) a compound of formula I, wherein R$^1$, R$^2$ and R$^3$ have the previously defined meanings, is saponified, if necessary, to obtain the compound of formula I wherein R$^1$ is OH;

(B) the compound obtained in step (A) is coupled to a solid phase support

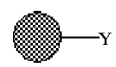

(by esterfication or amidation under appropriate conditions), wherein Y is a chemical precursor of X, thereby forming ester or amide bonds, respectively, depending on the type of reaction and the nature of Y.

If in step (A) R$^2$ is (1–8C)acyloxy, —O—C(O)—O-(1–6C)alkyl, —O—C(O)—O-(5–7C)aralkyl, R$^2$ may after step (B) subsequently be converted (by nucleophilic substitution reactions) into a halo atom, —SR$^6$ or —SeR$^6$, wherein R$^6$ is (1–6C)alkyl or (4–6C)aryl, optionally followed by oxidation to obtain the compounds of formula II wherein R$_2$ is —S(O)R$^6$ or —Se(O)R$^6$.

Other suitable processes for the preparation of the compositions of formula II are, for example, a Mitsunobu reaction with a compound of formula I wherein R$_1$ is OH, or a nucleophilic substitution reaction of a Merrifield-resin with a compound of formula I wherein R$_1$ is NR$_4$R$_5$ and at least one of R$_4$ or R$_5$ is hydrogen.

The use of the compounds and compositions of the present invention relates to the preparation of simple peptides and other small compounds and libraries thereof. A suitable method for the preparation of small molecules on a solid support, said small molecules being chemically removable therefrom upon application of a suitable mild cleaving agent, is characterized in that the method comprises the following steps:

(Aa) attaching to a solid phase support a compound having the formula I

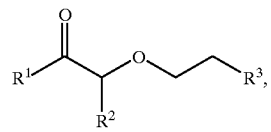

(I)

wherein

R$^1$ is hydroxy, (1–6C)alkoxy or NR$^4$R$^5$, R$^4$ and R$^5$ being independently hydrogen, (1–6C)alkyl, (3–7C) cycloalkyl, (2–6C)alkenyl, (4–6C)aryl or (5–7C) aralkyl, the aryl groups of which may be optionally substituted with halogen, (1–6C)alkyl or (1–6C) alkoxy;

R$^2$ is a halo atom, (1–8C)acyloxy, —O—C(O)—O-(1–6C)alkyl, —O—C(O)—O-(5–7C)aralkyl, —SR$^6$, —S(O)R$^6$, —SeR$^6$ or —Se(O)R$^6$, R$^6$ being (1–6C) alkyl or (4–6C)aryl; and R$^3$ is —Si(R$^7$)$_3$, R$^7$ being independently (1–6C)alkyl or (4–6C)aryl; to provide a composition of the formula II

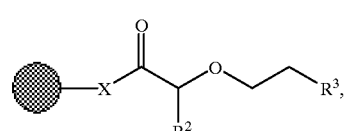

(II)

wherein the symbol

represents the solid phase support; X is a bond or a derivatizing group; and $R^2$, and $R^3$ have the previously defined meaning;

(Bb) substituting the $R^2$ group of the composition of formula II with an optionally protected ligand molecule, which ligand molecule is removable therefrom upon application of a mild (chemical) cleaving reagent.

After cleavage, isolation and purification of the resultant compounds can be effected, if desired, by any suitable separation or purification method known in the art, such as filtration, extraction, column chromatography, crystallization, distillation, and the like, or combinations of these methods. In the examples illustrating the present invention such procedures were used. However, a person skilled in the art will know which method to choose under the specific circumstances.

A preferred use of the compounds, compositions and methods of the present invention relates to the preparation of amino acids, simple (oligo)saccharides, heterocycles and steroids, originally possessing a suitable functionality available for attachment to the linker, such as, but not limited to, —OH, —$CO_2$H, —SH, —$NH_2$ or a monoprotected amino functionality. In particular preferred is the application of the present invention in the preparation of steroid compounds.

The term (1–8C)acyloxy means an acyloxy group having 1–8 carbon atoms, comprising an alkyl or ar(alk)yl moiety having the meaning as defined hereafter. Examples of acyloxy groups are formyloxy, acetyloxy (acetoxy), propionyloxy, butyryloxy, benzoyloxy and the like.

The term (1–6C)alkyl means a branched or unbranched alkyl group having 1 to 6 carbon atoms, such as methyl, ethyl, t-butyl, isopentyl, and the like. Preferred alkyl groups are (1–4C)alkyl groups, having 1–4 carbon atoms.

A (2–6C)alkenyl group is a branched or unbranched unsaturated hydrocarbon group having 2 to 6 carbon atoms. Examples are ethenyl, propenyl, allyl, and the like.

The term (1–6C)alkoxy means an alkoxy group having 1–6 carbon atoms, the alkyl moiety of which has the meaning as previously defined. Likewise, preferred alkoxy groups are (1–4C)alkoxy groups.

A (4–6C)aryl group is an aromatic moiety of 4 to 6 carbon atoms. The aryl group may further contain one or more hetero atoms, such as N, S, or O. Examples of aryl groups are phenyl, furanyl, and the like.

The term (5–7C)aralkyl means an aralkyl group having 5–7 carbon atoms, wherein the aryl group has the previously defined meaning. Examples are benzyl, methylenefuranyl, and the like. The preferred aralkyl group is the benzyl group.

The term (3–7C)cycloalkyl means a cycloalkyl group having 3–7 carbon atoms, being cyclopropyl, cyclobutyl, cyclopentyl, cyclohexyl or cycloheptyl. Cyclopentyl and cyclohexyl are preferred cycloalkyl groups.

The term combinatorial chemistry refers to an ordered strategy for the simultaneous (parallel or split & mix) synthesis of diverse compounds by sequential addition of reagents which leads to the generation of large chemical libraries. Thus, combinatorial chemistry also refers to the schematic and repetitive, connection of different varying structures to each other to yield arrays of diverse molecular entities.

A derivatizing group is a functionality enabling covalent attachment of the linker to the polymeric support. Preferably such derivatizing groups comprise an amine or hydroxy functionality or a polyether chain having an amine or a hydroxy functionality at the terminus. Examples of derivatizing groups are, but not limited to only these examples: —O—, —NH—, —O—$C_6H_4$—$CH_2$—O—, —($CH_2$$CH_2$O)$_4$—$CH_2$$CH_2$—NH—, and the like. With the term chemical precursor of a derivatizing group (Y) is meant any structure which at coupling with a linker is converted into a derivatizing group, such as —OH, —$NH_2$, —O—$C_6H_4$—$CH_2$—OH, —($CH_2$$CH_2$O)$_4$—$CH_2$$CH_2$—$NH_2$, and the like.

A library of molecules is an intentionally created collection of different compounds, also including a collection of stereoisomers, which can be prepared either synthetically or biosynthetically and screened for biological activity in a variety of different formats (e.g. libraries of soluble molecules; libraries of compounds thethered to resin beads, silica chips, or other solid supports).

A ligand molecule is any molecule which may be attached to a solid support, either to undergo subsequent chemical modifications or for being exposed to a receptor in a biological assay for recognition or binding.

A linker, linking group or spacer is any molecule or group that provides spatial distance between a support and a ligand molecule. A linker in this respect in particular refers to a molecule or a group of molecules attached to a polymeric support or linked to a polymeric support via a derivatizing group allowing cleavage from the polymeric support or the derivatizing group under precisely defined conditions.

Mild cleaving conditions are neither strongly basic nor strongly acidic. A mild cleaving method for removal of the ligand compound from the solid support or from the derivatizing group on the solid support is fluoridolysis under essentially neutral conditions, as described in T. W. Greene et al., *Protective Groups in Organic Synthesis,* 2nd Ed., John Wiley & Sons, Inc., New York (1991); P. J. Kocienski, *Protecting Groups,* Georg Thieme Verlag Stuttgart, New York (1994), e.g. using tetrabutylammonium fluoride (TBAF), CsF, LiBF$_4$ or KF, optionally in combination with sonification. Another mild cleaving method is the use of iodine in combination with photolysis.

A solid phase support for use in the present invention will be inert to the reaction conditions needed for the synthesis and/or modifications of the attached ligand molecule. As used herein, solid phase support is not limited to a specific type of support. Rather a large number of supports are available and are known to one of ordinary skill in the art. Solid phase supports include silica, resins, derivatized plastic films, glass beads, plastic beads, alumina gels etcetera. Further, a polymeric support refers to a material or group of materials consisting of repeating monomeric units, optionally alternating with other units, typically called copolymers, which may be cross-linked (e.g.: polysterene 1% divinylbenzene, polyethylene glycol (PEG)). The polymeric support itself may be attached to another support, e.g. beads or pins. A suitable solid support may be selected on the basis of desired end use and suitability for various synthetic protocols. For peptide syntheses for example, a solid support may refer to resins such as polystyrene or polysterene based resins (e.g. PAM-resin obtained from Bachem Inc., Peninsula Laboratories, etc.), POLYHIPE® resin (obtained from Aminotech, Canada), polyamide resin (obtained from Peninsula Laboratories), polysterene resin grafted with polyethylene glycol (Tentagel®, Rapp Polymere, Tübingen, Germany) or polydimethylacrylamide resin (obtained from Milligen/Bioresearch, California). For application in the present invention, preferred resins are hydroxymethyl resin, aminomethyl resin and Wang resin (obtained from Novabiochem), and further Tentagel S PHB and Tentagel S NH$_2$ (obtained from Rapp Polymere).

The invention is further illustrated by the following examples.

EXAMPLES

Examples 1 and 2 illustrate the preparation of compounds of formula I.

Examples 3, 5, 6 and 7 illustrate the preparation of compositions of formula II.

Examples 4, 8, 9, 10, 11, 12, 13 and 16 illustrate the coupling of different ligand molecules to the compositions of formula II.

Examples 14, 15 and 18 illustrate the removal of different ligand molecules, using mild cleaving methods.

In example 17 the ligand molecule is first chemically modified before removal from the solid phase support.

Abbreviations
Ac=acetyl
Bn=benzyl
t-Boc=tert-butoxycarbonyl
(t-)Bu=(tert-)butyl
DIPEA=N,N-diisopropylethylamine
DMAP=N,N-dimethylaminopyridine
DMF=N,N-dimethylformamide
Et=ethyl
FMOC=9-fluorenylmethoxycarbonyl
Leu=leucine
Me=methyl
NIS=N-iodosuccinimide
Ph=phenyl
Phth=phthalimide
TBAF=tetrabutylammonium fluoride
TfOH=trifluoromethanesulfonic acid
TMS=trimethylsilyl
TMU=tetramethylurea ⬤—OH = Hydroxymethyl resin ■—OH = Wang resin Typical experimental procedures Example 1.(a)

A mixture of methyl dimethoxyacetate (1) (8 mL, 65.5 mmol), glyoxylic acid monohydrate (5.8 g, 63 mmol) and p-toluenesulfonic acid monohydrate (60 mg, 0.32 mmol) was heated at 80° C. for 18 h. The resulting solution was cooled to 0° C. and phosphorus pentoxide (7.0 g, 49.3 mmol) was added. After heating for 4 h at 80° C., methyl glyoxylate (2) (7.9 g, 90 mmol) was obtained by distillation in 70% yield.

1.(b)

Freshly distilled methyl glyoxylate (2) (7.9 g, 90 mmol) was dissolved in dichloromethane (70 mL), immediately followed by the addition of 2-(trimethylsilyl)-ethanol (16 mL, 112 mmol). The resulting solution was stirred for 20 h. Evaporation in vacuo gave hemi-acetal 3 (13.5 g, 65 mmol) in 73% yield as a colourless oil.

$^1$H NMR (200 MHz, CDCl$_3$): 0.0 (s, 9 H, Si(CH$_3$)$_3$), 0.84–1.10 (m, 2 H, CH$_2$TMS), 3.64 (m, 1 H, HCHCH$_2$TMS), 3.81 (s, 3 H, OMe), 3.90 (m, 1 H, HCHCH$_2$TMS), 4.93 (s, 1 H, OCHO).

1.(c)

A solution of freshly prepared hemi-acetal 3 (13.5 g, 65 mmol), tert-butyl pyrocarbonate (16.5 g, 76 mmol) and N,N-dimethylaminopyridine (740 mg, 6.06 mmol) in dichloromethane (150 mL) was stirred for 1 h. The reaction was quenched with saturated aqueous sodium hydrogencarbonate (150 mL) and the water layer was extracted with dichloromethane (2×150 mL). The combined organic layers were dried over sodium sulfate. The crude product was purified by flash chromatography (ethyl acetate:heptane=10:90→30:70) giving acetal 4 (15.7 g, 40 mmol) in 78% yield as a colourless oil.

$^1$H NMR (200 MHz, CDCl$_3$): 0.0 (s, 9 H, Si(CH$_3$)$_3$), 0.87–1.12 (m, 2 H, CH$_2$TMS), 1.48 (s, 9 H, C(CH$_3$)$_3$), 3.74 (m, 1 H, HCHCH$_2$TMS), 3.79 (s, 3 H, OMe), 3.87 (m, 1 H, HCHCH$_2$TMS), 5.82 (s, 1 H, OCHO); $^{13}$C NMR (50 MHz, CDCl$_3$): −1.4, 18.0, 27.7, 52.8, 68.1, 83.5, 94.4, 152.2, 166.4.

Example 2

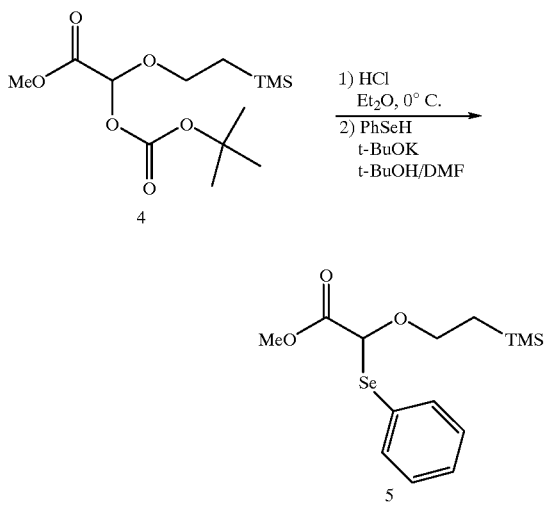

Hydrogen chloride was bubbled through a solution of acetal 4 (4.17 g, 13.6 mmol) in diethyl ether (50 mL) at 0° C. for 1 h and the resulting solution was concentrated in vacuo.

A suspension of benzeneselenol (1.5 mL, 14.1 mmol) and potassium tert-butoxide (1.65 g, 14.7 mmol) in tert-butanol (11.5 mL) was freshly prepared and N,N-dimethylformamide (5.6 mL) was added. This solution was added to the crude chloro-acetal and the resulting mixture was stirred for 3 h. The reaction was quenched with saturated aqueous sodium hydrogencarbonate (60 mL) and the water layer was extracted with diethyl ether (4×60 mL). The combined organic layers were dried over sodium sulfate. Purification over silica (ethyl acetate:heptane= 10:90→20:80; 1% triethylamine) gave selenoacetal 5 (2.6 g, 7.5 mmol) in 55% yield as a colourless oil.

$^1$H NMR (200 MHz, CDCl$_3$): 0.0 (s, 9 H, Si(CH$_3$)$_3$), 0.84–1.09 (m, 2 H, CH$_2$TMS), 3.57 (m, 1 H, HCHCH$_2$TMS), 3.63 (s, 3 H, OMe), 3.97 (m, 1 H, HCHCH$_2$TMS), 5.45 (s, 1 H, SeCHO), 7.29 (m, 3 H), 7.58 (m, 2 H); $^{13}$C NMR (50 MHz, CDCl$_3$): −1.3, 17.5, 52.4, 67.4, 80.9, 128.7, 129.2, 136.0.

Example 3

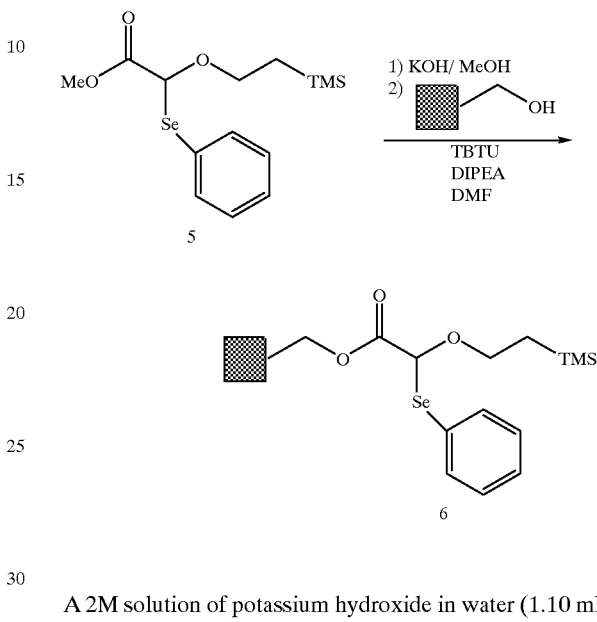

A 2M solution of potassium hydroxide in water (1.10 mL, 2.20 mmol) was added to a solution of selenoacetal 5 (375 mg, 1.08 mmol) in methanol (8 mL). The resulting solution was stirred for 3 h, after which it was cooled to 0° C. The solution was acidified with a 1M solution of hydrogen chloride in water (1.10 mL, 1.10 mmol) followed by the addition of N,N-diisopropylethylamine (200 mL, 1.14 mmol). Water (20 mL) and saturated aqueous sodium chloride (5 mL) were added and the water layer was extracted with dichloromethane (4×20 mL) containing N,N-diisopropylethylamine (4×200 μL). The combined organic layers were dried over sodium sulfate.

The crude product was dissolved in N,N-dimethylformamide (8 mL) and N,N-diisopropylethylamine (840 μL, 4.82 mmol), the Wang resin (250 mg, 0.24 mmol) and 2-(1H-benzotriazoyl-yl)-1,1,3,3-tetramethyluronium tetrafluoroborate (370 mg, 1.15 mmol) were added consecutively. The resulting suspension was shaken for 18 h. After filtration, resin 6 was washed with N,N-dimethylformamide (2×10 mL), water (2×10 mL), ethanol/water (3:1) (2×10 mL), ethanol (2×10 mL) and dichloromethane (3×10 mL), in this order. Total weight: 308 mg of resin-bound selenoacetal 6 (77% on gain of weight, 0.60 mmol/g). IR: 1751 cm$^{-1}$.

Example 4

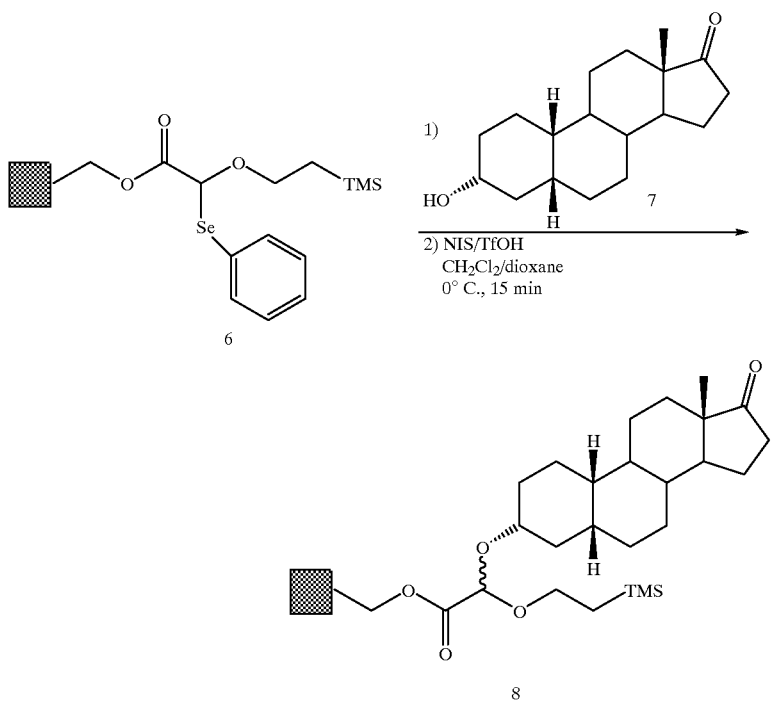

A solution of N-iodosuccinimide (112 mg, 0.50 mmol) and trifluoromethanesulfonic acid (8 mL, 0.09 mmol) in dichloromethane/dioxane (2.5 mL/2.5 mL) was freshly prepared. Part of this solution (1.8 mL) was added to a suspension of resin-bound selenoacetal 6 (300 mg, 0.18 mmol), steroid 7 (150 mg, 0.54 mmol) and 3 Å molecular sieves (4 beads) in dichloromethane (5 mL) at 0° C., and the resulting suspension was shaken for 15 min. The dark brown suspension was filtered and resin 8 was washed with dichloromethane (2×10 mL), 10% aqueous sodium thiosulfate (10 mL), water (2×10 mL), ethanol/water (3:1) (2×10 mL), ethanol (2×10 mL) and dichloromethane (3×10 mL), in this order.

Total weight: 309 mg of resin-bound steroid 8 (75% on gain of weight).

IR: 1740, 1754 $cm^{-1}$.

Example 5.(a)

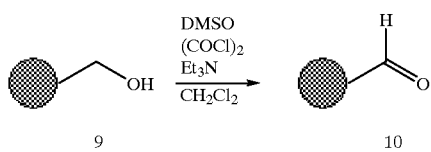

Oxallyl chloride (2.75 mL, 31.5 mmol) was added to a solution of dimethyl sulfoxide (2.30 mL, 32.4 mmol) in dichloromethane (160 mL) at −40° C. and the resulting solution was stirred for 15 min. Hydroxymethyl resin (9) (10 g, 9.8 mmol) was added and the resulting suspension was stirred for 1.5 h. Then, triethylamine (16 mL, 115 mmol) was slowly added and the resulting suspension was allowed to come to r.t. The reaction was quenched with ethanol (60 mL). The suspension was filtered and resin 10 was washed with saturated aqueous sodium hydrogencarbonate (100 mL), water (2×100 mL), ethanol/water (3:1) (2×100 mL), ethanol (2×100 mL) and dichloromethane (3×100 mL), in this order.

Total weight: 9.96 g of resin-bound aldehyde 10.

IR: 1705 $cm^{-1}$.

5.(b)

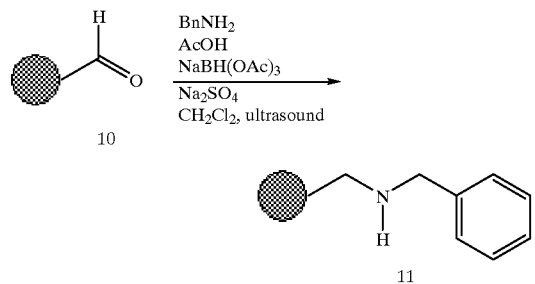

Benzylamine (12 mL, 110 mmol) was added to a suspension of resin-bound aldehyde 10 (9.96 g, 9.8 mmol) and sodium sulfate (10 g, 70 mmol) in dichloromethane (350 mL) and the resulting suspension was agitated by ultrasound for 5 min.

Acetic acid (10 mL, 175 mmol) was added to the suspension and the resulting suspension was agitated by ultrasound for 5 min.

Sodium triacetoxyborohydride was added in four portions of 2.5 g (11.8 mmol) with intervals of 1 h, during which the suspension was agitated by ultrasound. The reaction was quenched with triethylamine (25 mL, 179 mmol) followed by saturated aqueous sodium hydrogencarbonate (150 mL). The suspension was filtered and resin 11 was washed with water (2×100 mL), ethanol/water (3:1) (2×100 mL), ethanol (2×100 mL), N,N-diisopropylethylamine/dichloromethane (2×2.7 mL/100 mL) and dichloromethane (3×100 mL), in this order.

Total weight: 10.7 g of resin-bound amine 11 (85% on gain of weight; 0.78 mmol/g)

5.(c)

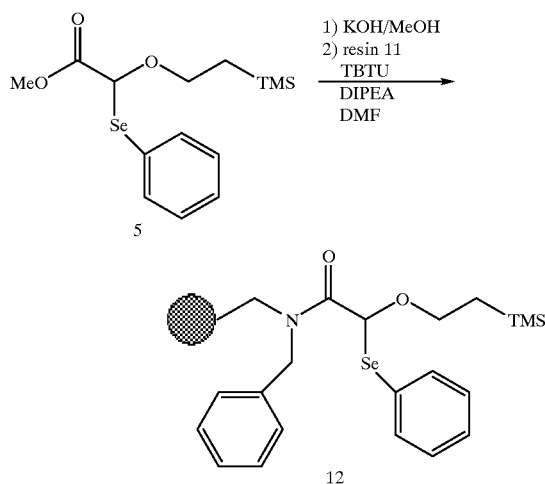

A 2M solution of potassium hydroxide in water (11.7 mL, 23.4 mmol) was added to a solution of selenoacetal 5 (4.04 g, 11.7 mmol) in methanol (80 mL). The resulting solution was stirred for 3 h, after which it was cooled to 0° C. The solution was acidified with a 1M solution of hydrogen chloride in water (11.7 mL, 11.7 mmol) followed by the addition of N,N-diisopropylethylamine (2 mL, 11.5 mmol). Water (160 mL) and saturated aqueous sodium chloride (40 mL) were added and the water layer was extracted with dichloromethane (4×160 mL) containing N,N-diisopropylethylamine (4×2 mL). The combined organic layers were dried over sodium sulfate.

The crude product was dissolved in N,N-dimethylformamide (80 mL) and N,N-diisopropylethylamine (9 mL, 51.7 mmol), resin 11 (3 g, 2.34 mmol) and 2-(1H-benzotriazoyl-yl)-1,1,3,3-tetramethyluronium tetrafluoroborate (4.0 g, 12.5 mmol) were added consecutively. The resulting suspension was shaken for 24 h. After filtration, resin 12 was washed with N,N-dimethylformamide (2×30 mL), water (2×30 mL), ethanol/water (3:1) (2×30 mL), ethanol (2×30 mL) and dichloromethane (3×30 mL), in this order.

Total weight: 3.63 g of resin-bound selenoacetal 12 (86% on gain of weight, 0.55 mmol/g).

IR:1652 cm$^{-1}$.

Example 6

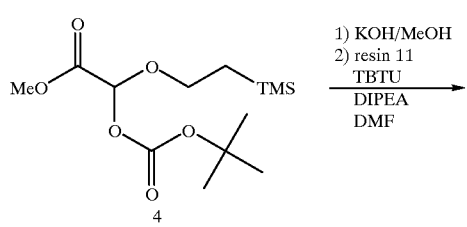

-continued

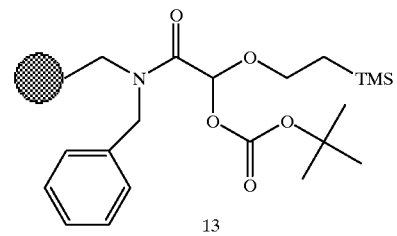

A 2M solution of potassium hydroxide in water (11.7 mL, 23.4 mmol) was added to a solution of acetal 4 (3.60 g, 11.7 mmol) in methanol (80 mL). The resulting solution was stirred for 3 h, after which it was cooled to 0° C. The solution was acidified with a 1M solution of hydrogen chloride in water (11.7 mL, 11.7 mmol) followed by the addition of N,N-diisopropylethylamine (2 mL, 11.5 mmol). Water (160 mL) and saturated aqueous sodium chloride (40 mL) were added and the water layer was extracted with dichloromethane (4×160 mL) containing N,N-diisopropylethylamine (4×2 mL). The combined organic layers were dried over sodium sulfate.

The crude product was dissolved in N,N-dimethylformamide (80 mL) and N,N-diisopropylethylamine (9 mL, 51.7 mmol), resin 11 (3 g, 2.34 mmol) and 2-(1H-benzotriazoyl-yl)-1,1,3,3-tetramethyluronium tetrafluoroborate (4.0 g, 12.5 mmol) were added consecutively. The resulting suspension was shaken for 24 h. After filtration, resin 13 was washed with N,N-dimethylformamide (2×30 mL), water (2×30 mL), ethanol/water (3:1) (2×30 mL), ethanol (2×30 mL) and dichloromethane (3×30 mL), in this order.

Total weight: 3.58 g of resin-bound acetal 13 (91% on gain of weight, 0.59 mmol/g).

IR: 1748, 1685 cm$^{-1}$.

Example 7

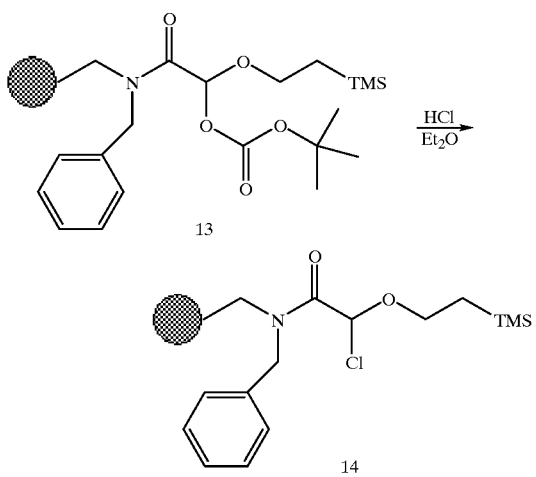

Hydrogen chloride was bubbled through a suspension of resin-bound acetal 13 (500 mg, 0.30 mmol) in diethyl ether (15 mL) at 0° C. for 1 h. The resulting suspension was filtered and washed with diethyl ether (3×15 mL).

Total weight: 471 mg of resin 14.

Cl analysis: 0.6 mmol/g.

IR: 1663 cm$^{-1}$.

Example 8

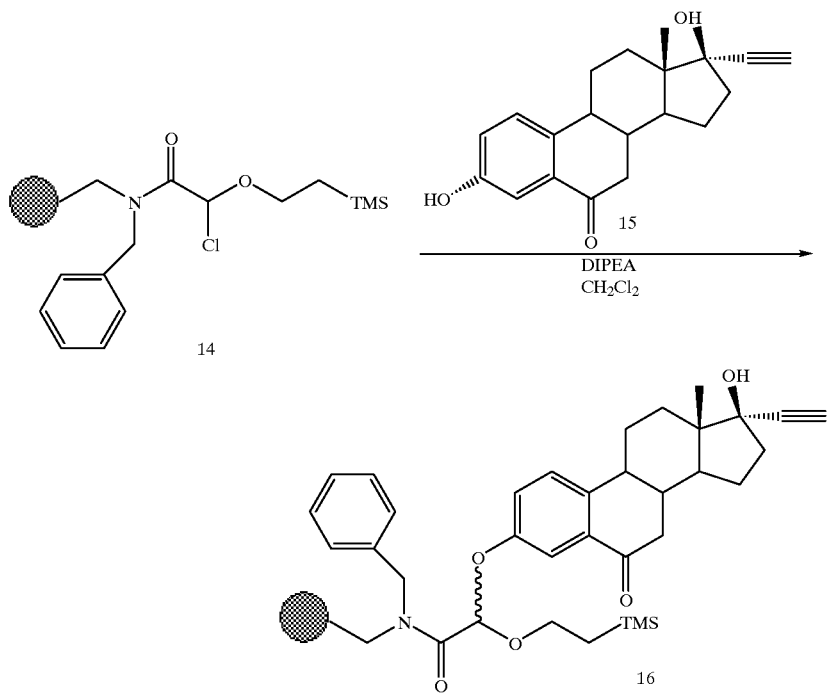

A suspension of resin-bound chloroacetal 14 (235 mg, 0.15 mmol), steroid 15 (310 mg, 1.00 mmol) and N,N-diisopropylethylamine (250 μL, 1.43 mmol) in dichloromethane (3 mL) was shaken for 72 h. The resulting suspension was filtered and resin 16 was washed with dichloromethane (2×5 mL), saturated aqueous sodium hydrogencarbonate (5 mL), water (2×5 mL), ethanol/water (3:1) (2×5 mL), ethanol (2×5 mL) and dichloromethane (3×5 mL), in this order.

Total weight: 267 mg of resin-bound steroid 16 (80% on gain of weight).

IR: 3302, 2100, 1684, 1654 cm$^{-1}$.

Example 9

N-Benzylglycine ethyl ester (17) (375 μL, 2.00 mmol) was added to a suspension of chloroacetal 14 (79 mg, 0.048 mmol) in dimethyl sulfoxide (1.00 mL) and the resulting suspension was shaken for 5 h. The suspension was filtered and resin 18 was washed with saturated aqueous sodium hydrogencarbonate (5 mL), water (2×5 mL), ethanol/water (3:1) (2×5 mL), ethanol (2×5 mL) and dichloromethane (3×5 mL), in this order.

Total weight: 85 mg of resin-bound benzylglycine ethyl ester 18 (83% on gain of weight).

IR: 1743, 1662 cm$^{-1}$.

Example 10

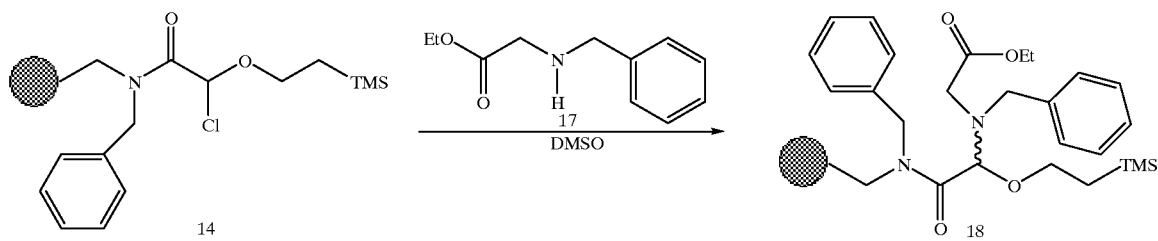

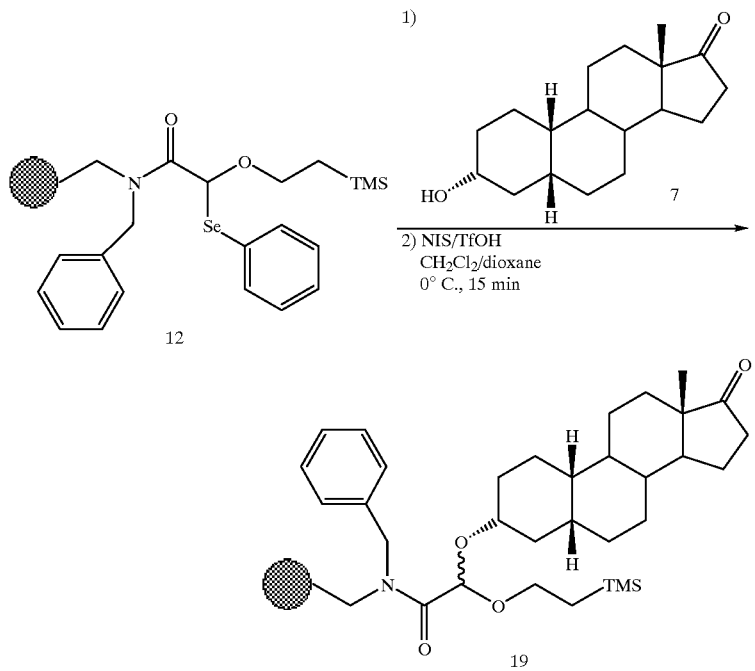

A solution of N-iodosuccinimide (68 mg, 0.30 mmol) and trifluoromethanesulfonic acid (5 µL, 0.06 mmol) in dichloromethane/dioxane (1.5 mL/1.5 mL) was freshly prepared. Part of this solution (1.3 mL) was added to a suspension of resin-bound selenoacetal 12 (200 mg, 0.12 mmol), steroid 7 (129 mg, 0.47 mmol) and 3 Å molecular sieves (4 beads) in dichloromethane (2.5 mL) at 0° C., and the resulting suspension was shaken for 15 min. The dark brown suspension was filtered and resin 19 was washed with dichloromethane (2×10 mL), 10% aqueous sodium thiosulfate (10 mL), water (2×10 mL), ethanol/water (3:1) (2×10 mL), ethanol (2×10 mL) and dichloromethane (3×10 mL), in this order.

Total weight: 209 mg of resin-bound steroid 19 (84% on gain of weight).

IR: 1740, 1650 cm$^{-1}$.

A solution of N-iodosuccinimide (225 mg, 1.00 mmol) and trifluoromethanesulfonic acid (16 µL, 0.18 mmol) in dichloromethane/dioxane (5 mL/5 mL) was freshly prepared. Part of this solution (0.65 mL) was added to a suspension of resin-bound selenoacetal 12 (100 mg, 0.055 mmol), sugar 20 (65 mg, 0.25 mmol) and 3 Å molecular sieves (4 beads) in dichloromethane (1.5 mL), and the resulting suspension was shaken for 1 h. The dark brown suspension was filtered and resin 21 was washed with dichloromethane (2×5 mL), 10% aqueous sodium thiosulfate (5 mL), water (2×5 mL), ethanol/water (3:1) (2×5 mL), ethanol (2×5 mL) and dichloromethane (3×5 mL), in this order.

Example 11

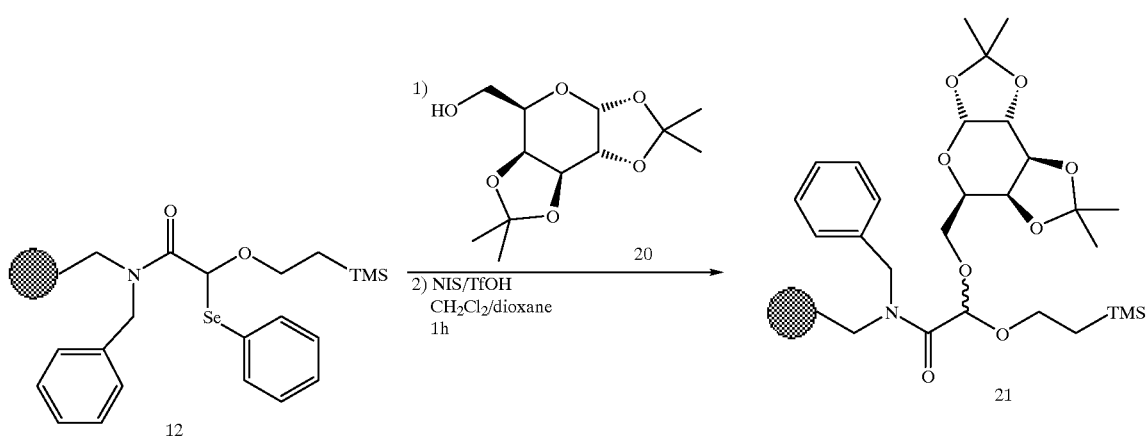

Total weight: 103 mg of resin-bound sugar 21 (80% on gain of weight).

IR: 1650 cm$^{-1}$.

Example 12

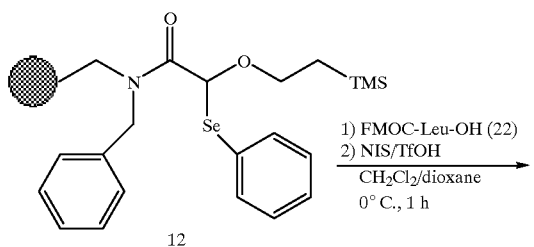

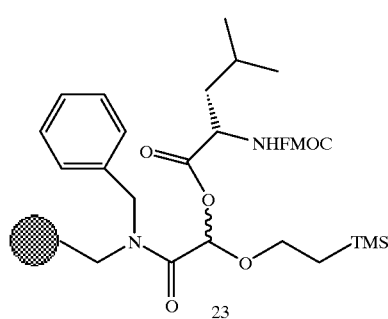

A solution of N-iodosuccinimide (225 mg, 1.00 mmol) and trifluoromethanesulfonic acid (16 μL, 0.18 mmol) in dichloromethane/dioxane (5 mL/5 mL) was freshly prepared. Part of this solution (1.3 mL) was added to a suspension of resin-bound selenoacetal 12 (200 mg, 0.11 mmol), FMOC protected amino acid 22 (170 mg, 0.48 mmol) and 3 Å molecular sieves (4 beads) in dichloromethane (2.5 mL) at 0° C., and the resulting suspension was shaken for 1 h. The dark brown suspension was filtered and resin 23 was washed with dichloromethane (2×10 mL), 10% aqueous sodium thiosulfate (10 mL), water (2×10 mL), ethanol/water (3:1) (2×10 mL), ethanol (2×10 mL) and dichloromethane (3×10 mL), in this order.

Total weight: 210 mg of resin-bound amino acid 23 (70% on gain of weight).

IR: 1755, 1730, 1658 cm$^{-1}$.

Example 13

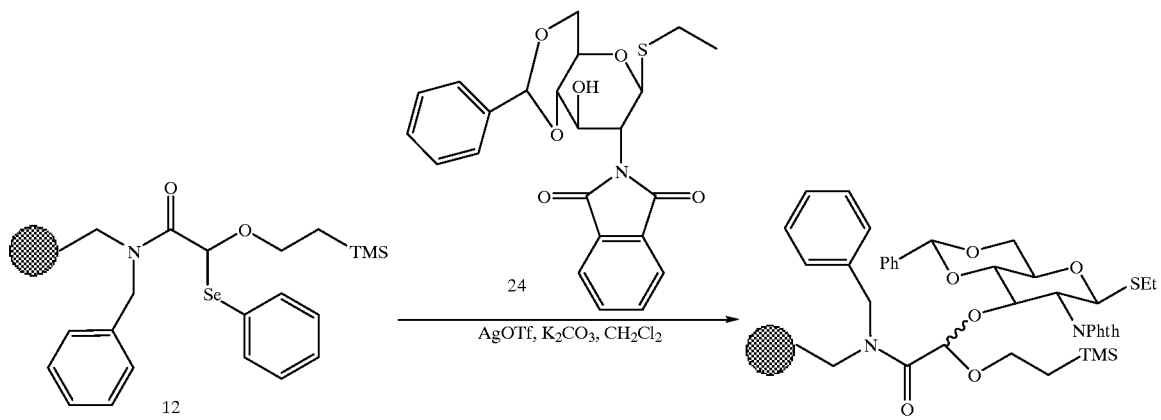

Silver triflate (45 mg, 0.175 mmol) was added to a suspension of resin-bound selenoacetal 12 (100 mg, 0.055 mmol), sugar 24 (200 mg, 0.45 mmol), potassium carbonate (10 mg, 0.072 mmol) and 4 Å molecular sieves (4 beads) in dichloromethane (2 mL) and the resulting suspension was shaken for 64 h, excluded from light. The resulting suspension was filtered and resin 25 was washed with dichloromethane (2×5 mL), 0.04M aqueous hydrogen chloride (5 mL), water (2×5 mL), 10% aqueous sodium thiosulfate (5 mL), water (2×5 mL), ethanol/water (3:1) (2×5 mL), N,N-dimethylformamide (2×5 mL) and dichloromethane (3×5 mL), in this order.

Total weight: 115 mg of resin-bound sugar 25 (97% on gain of weight).

IR: 1778, 1719, 1655 cm$^{-1}$.

Example 14

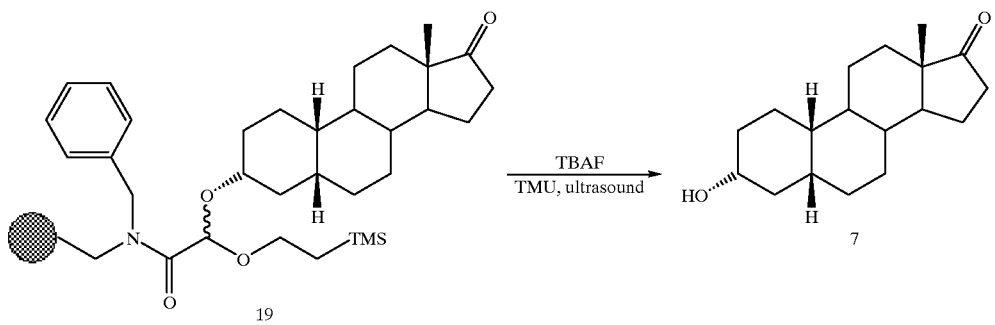

A suspension of resin-bound steroid 19 (102 mg, 0.040 mmol) and 3 Å molecular sieves (8 beads) in a 0.1M solution of tetrabutylammonium fluoride in tetramethylurea (1 mL) was agitated by ultrasound for 15 min. The resulting suspension was filtered and the resin and beads were washed with ethyl acetate (3×0.7 mL) and a 0.1M solution of tetrabutylammonium fluoride in tetramethylurea (1 mL). The latter was collected separately. This procedure was repeated three times (four cycles). The combined tetramethylurea/ethyl acetate-fractions were washed with aqueous sodium chloride (3×5 mL) and the crude product was purified by solid phase extraction (ethyl acetate:heptane=1:1) yielding steroid 7 (7.8 mg, 0.028 mmol) in 70% yield as a white solid.

$^1$H NMR was identical with a reference sample.

Example 15

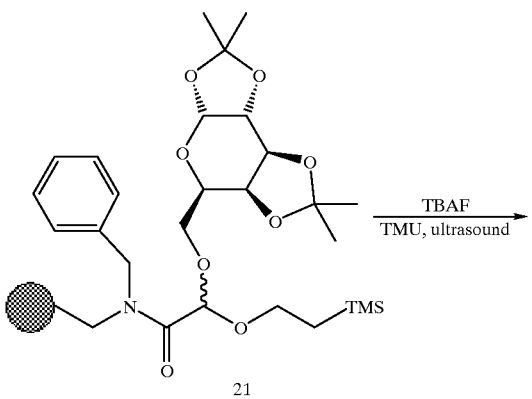

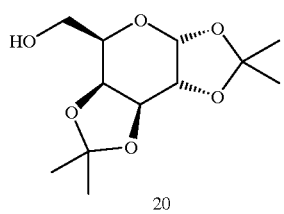

A suspension of resin-bound sugar 21 (50 mg, 0.02 mmol) and 3 Å molecular sieves (4 beads) in a 0.1M solution of tetrabutylammonium fluoride in tetramethylurea (0.5 mL) was agitated by ultrasound for 15 min. The resulting suspension was filtered and the resin and beads were washed with ethyl acetate (3×0.5 mL) and a 0.1M solution of tetrabutylammonium fluoride in tetramethylurea (0.5 mL). The latter was collected separately. This procedure was repeated three times (four cycles). The combined tetramethylurea/ethyl acetate-fractions were washed with aqueous sodium chloride (3×5 mL) and the crude product was purified by solid phase extraction (ethyl acetate:heptane=1:1) yielding sugar 20 (4 mg, 0.016 mmol) in 80% yield as a colourless oil.

$^1$H NMR was identical with a reference sample.

Example 16

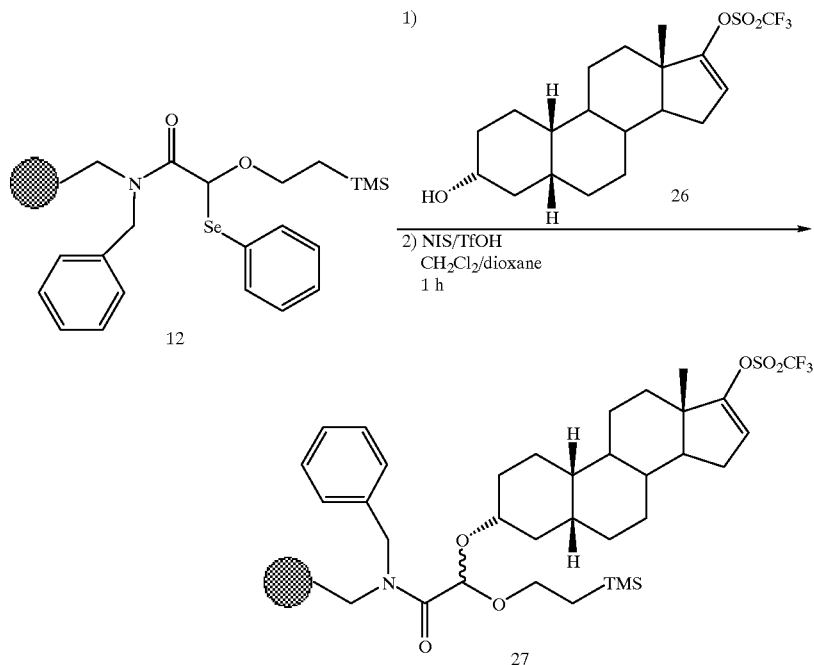

A solution of N-iodosuccinimide (225 mg, 1.00 mmol) and trifluoromethanesulfonic acid (16 μL, 0.18 mmol) in dichloromethane/dioxane (5 mL/5 mL) was freshly prepared. Part of this solution (6.5 mL) was added to a suspension of resin-bound selenoacetal 12 (600 mg, 0.33 mmol), steroid 26 (565 mg, 1.38 mmol) and 3 Å molecular sieves in dichloromethane (8 mL), and the resulting suspension was shaken for 1 h. The dark brown suspension was filtered and resin 27 was washed with dichloromethane (2×10 mL), 10% aqueous sodium thiosulfate (10 mL), water (2×10 mL), ethanol/water (3:1) (2×10 mL), ethanol (2×10 mL) and dichloromethane (3×10 mL), in this order.

Total weight: 630 mg of resin-bound steroid 27 (61% on gain of weight).

IR: 1740, 1215 cm$^{-1}$.

Example 17

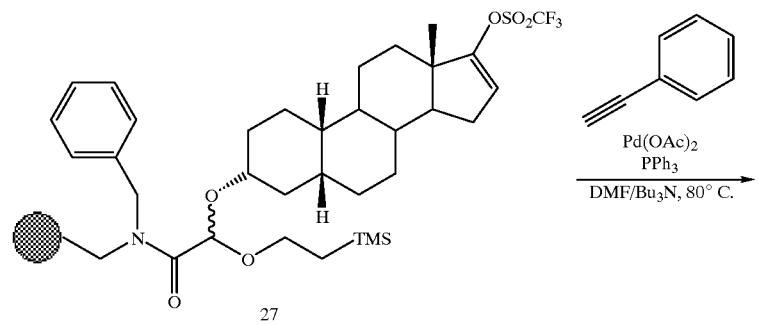

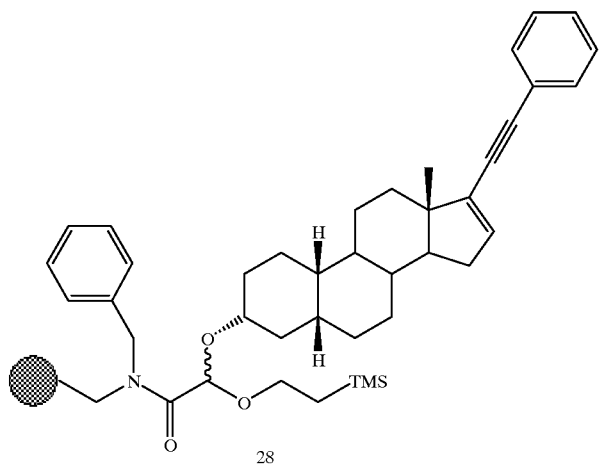

A solution of palladium(II)acetate (6 mg, 0.03 mmol) and triphenylphosphine (13 mg, 0.05 mmol) in N,N-dimethylformamide (2 mL) was added to resin-bound steroid 27 (48 mg, 0.015 mmol). Tributylamine (1.2 mL) and phenylacetylene (140 μL, 1.27 mmol) were added and the resulting suspension was kept at 80° C. for 2 h. Then, resin 28 was washed with N,N-dimethylformamide (2×2 mL), methanol (2×2 mL) and dichloromethane (3×2 mL).

Total weight: 49 mg of resin-bound steroid 28.

Example 18

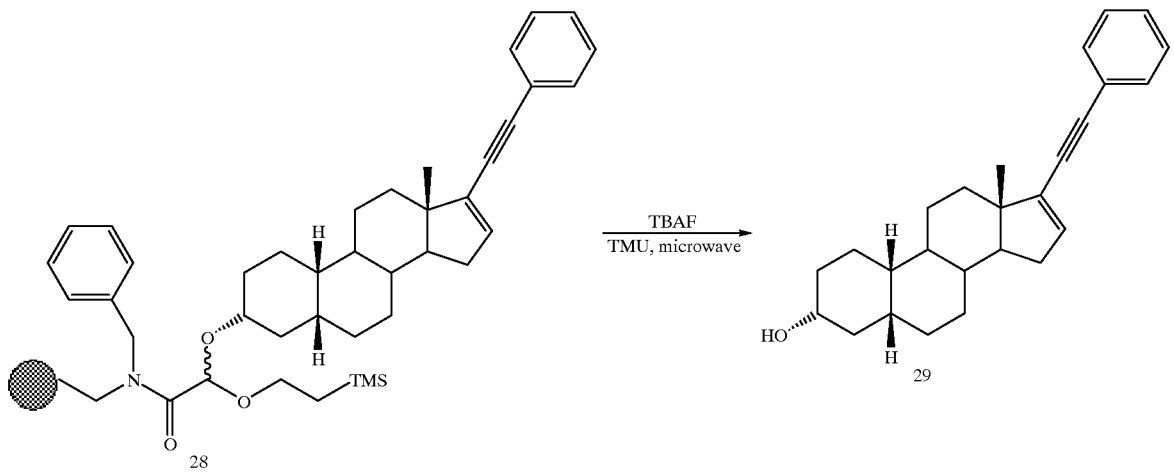

A 0.1M solution of tetrabutylammonium fluoride in tetramethylurea (0.5 mL) was added to resin-bound steroid 28 (49 mg) and the resulting suspension was agitated by microwaves for 60 min. The resulting suspension was filtered and the resin was treated under the same conditions three more times. The combined filtrates were concentrated in vacuo and the crude product was purified by solid phase extraction (ethyl acetate:heptane=1:1) yielding steroid 29 (2.4 mg, 0.007 mmol) in 44% overall yield as a white solid.

MS: ESI; m/z 361 [MH$^+$], 343 [MH$^+$-H$_2$O].

$^1$H NMR (200 MHz, CDCl$_3$): 0.90 (s, 3 H, 18-Me), 1.08–1.98 (m, 19 H), 1.96 (dd, 1 H, J 2, 11 Hz), 2.06 (dd, 1 H, J2, 11 Hz), 2.24 (ddd, 1 H, J3, 6.5, 16 Hz), 3.64 (m, 1 H, H-3), 6.09 (dd, 1 H, J2, 3.5 Hz), 7.29 (m, 3 H), 7.44 (m, 2 H).

I claim:
1. A compound having the formula I

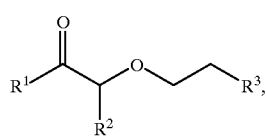

wherein
R$^1$ is hydroxy, (1–6C)alkoxy or NR$^4$R$^5$, R$^4$ and R$^5$ being independently hydrogen, (1–6C)alkyl, (3–7C)

cycloalkyl, (2–6C)alkenyl, (4–6C)aryl or (5–7C) aralkyl, the aryl groups of which may be optionally substituted with halogen, (1–6C)alkyl or (1–6C) alkoxy;

$R^2$ is a halo atom, (1–8C)acyloxy, —O—C(O)—O-(1–6C)alkyl, —O—C(O)—O-(5–7C)aralkyl, —SR$^6$, —S(O)R$^6$, —SeR$^6$ or —Se(O)R$^6$, R$^6$ being (1–6C) alkyl or (4–6C)aryl; and $R^3$ is —Si(R$^7$)$_3$, R$^7$ being independently (1–6C)alkyl or (4–6C)aryl.

2. The compound of claim 1, wherein R$^3$ is SiMe$_3$, SiEt$_3$, SiMe$_2$t-Bu or SiMe$_2$Ph.

3. The compound of claim 1, wherein R$^1$ is hydroxy or (1–6C)alkoxy.

4. The compound of claim 1, wherein R$^2$ is a halo atom, —O—C(O)—O-(1–6C)alkyl or —SeR$^6$.

5. The compound of claim 1, wherein R$^1$ is methoxy; R$^2$ is chlorine, —O—C(O)—O-t-Bu or —Se-phenyl; and R$^3$ is —SiMe$_3$.

6. A method for the preparation of a compound having the formula I

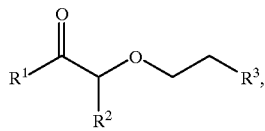

(I)

wherein R$^1$, R$^2$ and R$^3$ having the meanings defined in claim 1, comprising the step of protecting/activating the hydroxy functionality of a compound of formula Ib

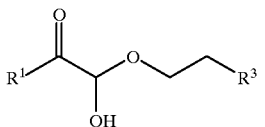

(Ib)

thereby forming the compounds of formula I wherein R$^2$ is (1–8C)acyloxy, —O—C(O)—O-(1–6C)alkyl, or —O—C(O)—O-(5–7C) aralkyl.

7. A composition having the formula II

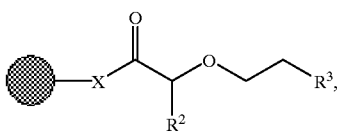

(II)

wherein the symbol

represents a solid phase support; X is derivatizing group comprising N or O;

$R^2$ is a halo atom, (1–8C)acyloxy, —O—C(O)—O-(1–6C)alkyl, —O—C(O)—O-(5–7C)aralkyl, —SR$^6$, —SeR$^6$ or —Se (O)R$^6$, R$^6$ being (1–6C)alkyl or (4–6C) aryl; and $R^3$ is —Si(R$^7$)$_3$, R$^7$ being independently (1–6C)alkyl or (4–6C) aryl.

8. The composition of claim 7, wherein R$^3$ is SiMe$_3$, SiEt$_3$, SiMe$_2$t-Bu or SiMe$_2$Ph.

9. The composition of claim 7, wherein R$^2$ is a halo atom, —O—C(O)—O-(1–6C)alkyl or —SeR$^6$.

10. The composition of claim 7, wherein R$^2$ is chlorine, —O—C(O)—O-t-Bu or —Se-phenyl; and R$^5$ is —SiMe$_3$.

11. A method for the preparation of a composition having the formula II

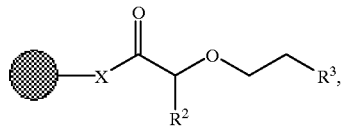

(II)

wherein the symbol

X, and R$^2$ and R$^3$ have the meanings defined in claim 7, comprising the following steps:
(A) saponifying, if necessary, a compound of formula I of claim 1, wherein R$^1$ and R$^2$ and R$^3$ having the meanings defined in claim 1, to obtain the compound of formula I wherein R$^1$ is OH; and
(B) coupling the compound obtained in Step (A) to a solid phase support

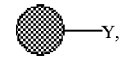

wherein Y is a chemical precursor of X.

12. A method for the preparation of small molecules on a solid support, said small molecules being chemically removable therefrom upon application of a cleaving agent, wherein the method comprises the following steps:
(A) attaching to a solid phase support a compound having the formula I

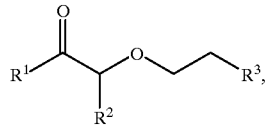

(I)

wherein
$R^1$ is a hydroxy, (1–6C)alkoxy or NR$^4$R$^5$, R$^4$ and R$^5$ being independently hydrogen, (1–6C)alkyl, (3–7C) cycloalkyl, (2–6C)alkenyl, (4–6C)aryl or (5–7C) aralkyl, the aryl groups of which may be optionally substituted with halogen, (1–6C)alkyl or (1–6C) alkoxy;

$R^2$ is a halo atom, (1–8C)acyloxy, —O—C(O)—O-(1–6C)alkyl, —O—C(O)—O-(5–7C)aralkyl, —SR$^6$, —S(O)R$^6$, —SeR$^6$ or —Se(O)R$^6$, R$^6$ being (1–6C) alkyl or (4–6C) aryl; and $R^3$ is —Si(R$^7$)$_3$, R$^7$ being independently (1–6C)alkyl or (4–6C) aryl; to provide a composition of the formula II

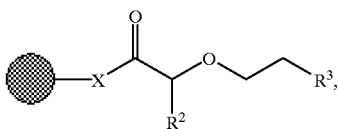
(II)

wherein the symbol

represents a solid phase support; X is a derivatizing group comprising N or O; and $R^2$, and $R^3$ have the meaning defined above; and (B) substituting the $R^2$ group of the composition of formula II with an optionally protected ligand molecule, which ligand molecule is removable therefrom upon application of a cleaving agent.

13. The method of claim 6, wherein the protecting/activating step is followed by substituting a halogen for the protected/activated hydroxy group by nucleophilic substitution.

14. The method of claim 13, further comprising replacing the halogen by —$SR^6$ or —$SeR^6$, $R^6$ being (1–6C)alkyl or (4–6C) aryl, by nucleophilic substitution.

15. The method of claim 14, further comprising oxidizing the resulting compound to obtain compounds of formula I wherein $R^2$ is —$S(O)R^6$ or —$Se(O)R^6$.

16. The compound of claim 2, wherein $R^1$ is hydroxy or (1–6C)alkoxy.

17. The compound of claim 2, wherein $R^2$ is a halo atom, —O—C(O)—O-(1–6C)alkyl or —$SeR^6$.

18. The compound of claim 3, wherein $R^2$ is a halo atom, —O—C(O)—O-(1–6C)alkyl or —$SeR^6$.

* * * * *